US006376566B1

(12) United States Patent
Bergeron et al.

(10) Patent No.: US 6,376,566 B1
(45) Date of Patent: Apr. 23, 2002

(54) AGRICULTURAL FOAM MARKER COMPOSITIONS AND USE THEREOF

(75) Inventors: Vance Bergeron, Lyons (FR); Robert J. Riedemann, Neptune, NJ (US); Rajeev Subramanyam, Hoboken, NJ (US); Joel M. Coret, Robbinsville, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 09/593,738

(22) Filed: Jun. 14, 2000

(51) Int. Cl.$^7$ .................................................. C08J 9/30
(52) U.S. Cl. ..................... 521/65; 47/1.5; 47/2; 521/78
(58) Field of Search .......................... 47/1.5, 2; 521/65, 521/78

(56) References Cited

U.S. PATENT DOCUMENTS

| | | | |
|---|---|---|---|
| 3,912,665 A | 10/1975 | Spitzer et al. | 521/79 |
| 3,912,666 A | 10/1975 | Spitzer et al. | 521/78 |
| 4,228,048 A | 10/1980 | Tesdahl | 260/17.4 |
| 4,417,016 A | 11/1983 | Cline et al. | 521/65 |
| 4,425,440 A | 1/1984 | Bloembergen | 521/78 |
| 4,442,018 A | 4/1984 | Rand | 252/307 |
| 4,472,230 A | 9/1984 | Sachs et al. | 521/78 |
| 4,795,590 A | 1/1989 | Kent et al. | 252/307 |
| 4,874,641 A | 10/1989 | Kittle | 424/244 |
| 4,990,373 A | 2/1991 | Kittle | 427/244 |
| 5,026,735 A | 6/1991 | Stern | 521/50 |
| 5,096,616 A | 3/1992 | Kittle | 252/307 |
| 5,133,500 A | 7/1992 | Simpson | 239/150 |
| 5,205,290 A | 4/1993 | Unger | 521/65 |
| 5,434,192 A | 7/1995 | Thach et al. | 521/50 |
| 5,570,539 A | 11/1996 | Smith, Jr. | 47/1.5 |
| 5,597,793 A | 1/1997 | Besse et al. | 510/434 |
| 5,992,758 A | 11/1999 | Mack | 239/159 |

FOREIGN PATENT DOCUMENTS

WO    WO 99/44648    9/1999    .......... A61L/15/60

*Primary Examiner*—Morton Foelak
(74) *Attorney, Agent, or Firm*—George W. Rauchfuss; John A. Shedden

(57) ABSTRACT

Aqueous agricultural foam marker compositions for delineating treated from untreated areas comprise a foamable composition of an anionic surfactant which is an α-olefin sulfonate and/or an alkyl ether sulfate, a linear $C_{12-16}$ alkanol, a foam stabilizing polymer, and one or more solvents. The foams produced from the foamable compositions have increased foam life, enhanced wind resistance, and are producable over a wide range of soft/hard water conditions.

17 Claims, No Drawings

AGRICULTURAL FOAM MARKER COMPOSITIONS AND USE THEREOF

FIELD OF THE INVENTION

This invention relates to agricultural foam marker compositions and concentrates thereof and their use in agriculture to generate foam markers to delineate a line on soil or a field or on crops for marking the edges of areas already agriculturally processed or treated.

BACKGROUND OF THE INVENTION

In modern agriculture, large areas are to be treated at a time, such as by cultivating the soil, seeding the soil or applying fertilizer, herbicides, insecticides, pesticides and the like. In such agricultural operations farm sprayers, chemical application, seeders, cultivators and other machinery is drawn or propelled over large ground areas. It is essential for a variety of reasons, including economy of time and materials, ecology, efficiency and maximization of treatment or coverage, that the areas being treated be clearly marked or delineated to distinguished the treated area from untreated or not yet treated areas.

In general, an area of agricultural ground, soil or crops is treated by the use of tractors, cultivators, seeders, sprayers, chemical applicators and other farming equipment that is drawn or propelled over the ground. In operating the equipment, it is generally essential that the area treated by operation of the equipment be as contiguous as practical to the area already being treated so as to avoid gaps in treatment or overlap in treatment. If an area is left untreated, crop loss can result. On the other hand, overlapping of areas of treatment can result in wasteful use of the material being used to treat the area as well as harmful excess deposit of such materials into areas of overlap. To avoid both untreated areas and areas being subjected to overlapping treatment it has become necessary to ensure an adequate marking system for delimiting treated from untreated areas.

For this purpose, there have been various proposals for obtaining such delineating or marking of areas treated. Among these proposals are the use of various mechanical marking devices and various electronic sensing devices. Among the most numerous proposals and most generally used is the use of sprayed dyes or foams for marking the edges of treated areas.

Mechanical systems involve undesirable use of manpower, and in many instances result in crop damage, and are generally economically undesirable and not a particularly effective means of marking the areas of treatment. The use of marking dyes is generally not ecologically desirable nor does it generally provide sufficient visible marking.

The use of marking foams generally involves the deposit of a foam marker at the edge of the treated areas to enable the operator of the treating equipment to adjust the operation of the treating equipment to obtain contiguous but not overlapping areas of treatment. In operation, a foam marker composition is employed for this purpose. Foam is generated from a tank of a foam marker composition by use of pressurized gas, generally air, and the foam is deposited at the edge of a treated area by being dropped along that edge from the end of a sprayer boom attached to a tractor or other treating equipment. In this manner, the operator of the tractor or equipment can visually determine the edge of a previously treated area by observing the deposited foam and the operator can then adjust the direction and position of the treatment equipment so that it operates in a contiguous but not overlapping manner.

A wide variety of agricultural foam marker compositions have been marketed for this purpose. However, the agricultural foam marker composition commercially available suffer from various drawbacks. For example, such compositions may not be suitable for use with both soft water (about 50 ppm $CaCO_3$) and hard water (about 1100 or more ppm $CaCO_3$). Similarly, such compositions may not produce suitable foam markers under a variety of environmental conditions, such as hot or cold, humid or dry and calm or windy conditions. Additionally, such compositions may not produce foam markers that are stable and that last long enough, i.e. for at least about 45 minutes at 25° C. when produced using hard water, and for at least about 1 hour at 25° C. when produced using soft water.

SUMMARY OF THE INVENTION

In accordance with this invention, aqueous agricultural foam marker formulations are provided that can produce acceptable foams in both hard and soft water that are long lasting and have improved wind resistance. Another aspect of this invention providing foamable aqueous agricultural foam marker concentrate compositions for dilution with water at a ratio of about 1:75 to about 1:100 or more to provide the aforementioned foam marker formulations. A further aspect of this invention is to provide an improved method of depositing a foam marker at the edge of an agriculturally treated area to distinguish or delimit treated area from untreated area by depositing foam markers produced from the aforementioned foam marker formulations of this invention.

The improved ready-to-use aqueous foam marker formulations of this invention comprise from about 0.10 to about 0.40 wt % of at least one anionic surfactant selected from salts of an α-olefin sulfonate having from about 12 to about 16 carbon atoms and salts of an alkyl ether sulfate having from about 8 to about 16 carbon atoms; from about 0.03 to about 0.20 wt % of a foam stabilizing polymer selected from a polyacrylic acid and salt thereof having a molecular weight of from about 10,000 to about 500,000, an ethylene oxide/propylene oxide block copolymer having a molecular weight up to about 30,000, a polyethylene glycol having a molecular weight of 400 or greater, and a biopolymer having a molecular weight of about 100,000 or greater; optionally from about 0.04 to about 0.08 wt % of at least one linear alkanol having from about 12 to about 16 carbon atoms; optionally, from about 0.05 to about 0.40 wt % of one or more solvents selected from 2 butoxyethanol, diethylene glycol, dipropylene glycol, ethanol, propanol, isopropanol and butanol, and water, wherein the weight percents are based on the total weight of the ready-to-use formulation and the weight percents of the anionic surfactant is on a dry weight basis of the surfactant.

Concentrate compositions for producing the improved ready-to-use aqueous foam marker formulations of this invention comprise from about 10 to about 40 wt % of at least one anionic surfactant selected from salts of an α-olefin sulfonate having from about 12 to about 16 carbon atoms and salts of an alkyl ether sulfate having from about 8 to about 16 carbon atoms; from about 3 to about 20 wt % of a foam stabilizing polymer selected from a polyacrylic acid and salt thereof having a molecular weight of from about 10,000 to about 500,000, an ethylene oxide/propylene oxide block copolymer having a molecular weight up to about 30,000, a polyethylene glycol having a molecular weight of 400 or greater, and a biopolymer having a molecular weight of about 100,000 or greater; from about 4 to about 8 wt % of at least one linear alkanol having from about 12 to about 16 carbon atoms; from about 5 to about 40 wt % of one or more solvents selected from 2 butoxyethanol, diethylene glycol, dipropylene glycol, ethanol, propanol, isopropanol and butanol, and water, wherein the weight percents are based on the total weight of the concentrate composition and the weight percents of the anionic surfactant is on a dry weight basis of the surfactant.

Such ready-to-use formulations can be prepared by combining, in sufficient water, the aforementioned necessary and optional ingredients at the time of intended use, or can be formulated from foamable aqueous agricultural foam marker concentrate compositions by diluting the concentrate compositions with about 75 to about 100 parts or more, preferably about 100 parts, of water per part of concentrate composition. Preferably, the ready-to-use formulations are prepared from concentrate compositions.

DETAILED DESCRIPTION OF THE INVENTION

The anionic surfactant(s) present in the agricultural foam marker compositions and formulations of the invention are α-olefin sulfonates and/or alkyl ether sulfates. The α-olefin sulfonate are salts of a monovalent cation which can be an alkali metal ion, such as sodium, lithium or potassium, an ammonium ion or an alkyl-substituent or hydroxyalkyl substitute ammonium in which the alkyl substituents may contain from 1 to 3 carbon atoms in each substituent. The α-olefin moiety has from 12 to 16 carbon atoms. The alkyl ether sulfate surfactants are also salts of the aforementioned monovalent cations. The alkyl ether sulfate may be an alkylpolyether sulfate and contains from 8 to 16 carbon atoms in the alkyl ether moiety. Preferred as anionic surfactants are sodium lauryl ether sulfate (2–3 moles ethylene oxide), $C_8$–$C_{10}$ ammonium ether sulfate (2–3 moles ethylene oxide) and a $C_{14-16}$ sodium α-olefin sulfonate and mixtures thereof.

The foam stabilizing polymer employed in the concentrate compositions and formulations of this invention use any suitable polyacrylic acid polymer having a molecular weight of from about 10,000 to about 500,000, any suitable ethylene oxide/propylene oxide block copolymer having a molecular weight up to about 30,000, any suitable polyethylene glycol having a molecular weight of 400 or greater, or any suitable biopolymer having a molecular weight of about 100,000 or more, preferably about 1,000,000 or more. The polymer increases the foam stability by retarding water drainage, reducing water evaporation and increasing the mechanical strength of the foam.

Any suitable polyacrylic and polymer may be employed in this invention. olyacrylic acid polymers are commercially available from a variety of sources. The polyacrylic acid polymers are of the type identified in Chapter 17 of the *Handbook of Water Soluble Gums and Resins*, by R. L. Davidson, McGraw Hill 1980.

The ethylene oxide/propylene oxide block copolymers are also commercially available polymers. As an example of such polymers, there can be mentioned ANTAROX polymers, such as ANTAROX F-88 block copolymer from Rhodia, Inc.

The biopolymer may be a water dispersible or soluble hydrophilic colloid selected form the group consisting of gum ghatti, gum arabic, gum tragacanth, locust bean gum, gum karaya, guar gum, carrageenan, algin, xanthan gum and welan gum, and mixtures thereof. These polymers may be used unmodified, as normally isolated from their source materials, or they may be modified as is well known in the polymer art such as by hydroxyalkylation, carboxyalkylation, or mixed hydroxyalkylation carboxyalkylation. Specific examples of modified polymers are carboxymethyl-2-hydroxy-propylpropyl-ether guar gum and 2-hydroxy-3-(trimethyl ammonio) propyl-ether chloride guar gum. Many of these derivatives form clear solutions in water. Thus, the term water-soluble polymer is intended to mean polymers which form colloidal solutions or colloidal dispersions in water.

The sources of these gums are well known. Gum ghatti is derived from an exudate of the *Anogeissus latifolia* tree of the Combretaccae family. Gum arabic is derived from an exudate of the acacia tree. Gum tragacanth is derived from an exudate of various species of shrubs belonging to the genus Astragalus. Gum karaya is derived form an exudate of the *Sterculia ureus* tree. Locust bean gum is derived form the fruit of the carbo tree (*Ceratonia siligua*). Guar gum is derived form the seeds of two annual leguminous plants, *Cyamopsis tetragonalobus and Cyamopsis psoraloides*. Algin is derived from all brown seaweeds, of the family Phaeophyceae, although principally from the giant kelp *Macrosystis pyrifera*. Carrageenan is derived form certain species of red seaweeds of the Gigartinaceae, Solieriaceae, Phylphoraceae, and Hypneaceae families.

Commercially available xanthan gum biopolymers can be obtained form Kelco Div., Merck & Co., Inc. under the trademark of "Keizan" or from Pfizer, Inc. under the trademark of "Flocon". Welan gum is a polymer made by an Alcaligenes bacteria identified as S-130. Welan gum is commercially available under the trade name BIO-ZAN® from Kelco Div., Merck & Co., Inc. Commercially available guar and modified guar gums are available from Rhodia, Inc. under the trade name JAGUAR.

Accordingly, the biopolymer may comprise natural and modified natural gums such as gum ghatti, gum arabic, gum tragacanth, locust bean gum, gum karaya, guar gum, carrageenan, algin, biopolymers such as xanthan gum or Welan gum and the hydroxyethyl, carboxymethyl, hydroxyethyl carboxymethyl and hydroxypropyl ether derivatives thereof, and mixtures thereof. Preferred biopolymers for use in this invention are guar and xanthan gums and derivatives thereof.

While the linear alkanol having from about 12 to about 16 carbon atoms and at least one solvent components are optional in the ready-to-use formulations that are prepared at the time of intended use, these components are present in the aqueous concentrate compositions intended for storage until such time as the concentrate is to be diluted to form ready-to-use foamable formulations.

The linear alkanol is a linear alcohol having from about 12 to about 16 carbon atoms and is present in the concentrate composition in an amount of from about 4 to about 8 at %, preferably from about 4 to about 6 at %, and thus in the 1:100 diluted formulation in an amount of from about 0.04 to about 0.08, preferably from about 0.04 to about 0.08 wt %.

The at least one organic solvent is generally present in the concentrate composition in an amount of from about about 5 to about 40 wt %, preferably from about 15 to about 35 wt %, and thus is present in the 1:100 diluted formulation in an amount of from about 0.05 to 0.40, preferably from about 0.15 to about 0.35 wt %. While the solvent may comprise at least one of 2 butoxyethanol, diethylene glycol, hexylene glycol, dipropylene glycol, ethanol, propanol, isopropanol or butanol, the solvent is preferably 2-butoxyethonol, or a mixture of 2 butoxyethanol, diethylene glycol and isopropanol.

Any other suitable optimal components may be present in minor amounts in the concentrate compositions or the ready-to-use formulations, such as for example, chelates, bactericides and the like. Any suitable chelating agent may be employed, such as, for example, chelating agents such as citric acid, sodium EDTA, sodium tripolyphosphate, phosphoric acid and the like. The chelating agent will generally be present in the concentrate composition in an amount up to about 10 wt %, preferably up to about 5 wt %, and thus be present in the ready-to-use formulation in an amount of up to about 0.10 wt %, preferably in an amount up to about 0.05%.

For producing the foam markers, a suitable tank mix (ready-to-use mix) is prepared either by suitable dilution of a concentrate composition or forming the tank mix by mixing the necessary components in a suitable amount of water in a tank or suitable vessel or container. It is preferred that the components be of low viscosity, i.e. of less than about 300 cPs, preferably less than about 200 cPs, and readily dissolvable in water without mixing since generally, the equipment operator may not have mixing equipment readily available. The tank, vessel or container with the ready-to-use formulation therein is provided with a suitable source of inert gas, preferably air, for forming a foam from the formulation. In general, any suitable amount of inert gas or air may be employed. For example, a suitable foam for use as a foam marker of this invention may be generated with air at a flow rate of 76.8 liter/min. and formulation liquid at a flow rate of about 0.5 liter/min.

The resulting foam markers produced from the concentrate compositions and formulations of this invention are characterized by improved longevity (time to disappearance) and resistance to wind (time to being blown away) compared to presently available commercial agricultural foam marker products. That is, as comparison to commercial products the foam markers produced according to this invention have increased time to disappearance at temperatures up to about 55° C. and at ambient outdoor temperature of about 25° C. Additionally, the foam markers produced according to this invention produce longer times until the foam marker is blown away by wind (e.g., wind at a face velocity of about 600–700 ft/min) than comparative commercial products.

The foamable aqueous agricultural foam marker concentrate compositions of this invention are characterized by improved shelf life of up to about 1 year or more. Additionally, the concentrate compositions and the formulations of this invention can be formulated with either hard water (at least 1100 pm $CaCO_3$) or soft water (about 50 ppm $CaCO_3$). If formulated in soft water, the foam markers of this invention are generally characterized by a longevity at 55° C. of greater than 30 minutes and a longevity at 25° C. of at least about 1 hour, and if formulated in hard water evidence a longevity at 55° C. of greater than 25 minutes and a longevity at 25° C. of at least about 45 minutes or more.

The invention is illustrated by the following illustrative, but non-limiting, examples. In the examples, the percentages are percent by weight unless specified otherwise. The term "a.i." refers to "active ingredient".

EXAMPLE 1 to 7

Ready-to-use tank mixes of seven foam marker formulations of this invention were prepared, their performance was compared to ready-to-use tank mixes of two commercially available foam marker formulations identified as Comparative Compositions A and B. The formulations of this invention were as follows.

Formulation 1:
  80% $C_{14-16}$ Sodium α-olefin sulfonate (40% a.i.)
  50% Xanthan gum (Rhodigel EZ)
  15% Water
Formulation 2:
  80% $C_{14-16}$ Sodium α-olefin sulfonate (40% a.i.)
  5% Hydroxypropyl guar MS-1-2(Jaguar HP 120)
  15% Water
Formulation 3:
  80% $C_{14-16}$ Sodium α-olefin sulfonate (40% a.i.)
  5% Hydoxypropyl guar MS-0.9 (Jaguar HB 160)
  15% Water
Formulation 4:
  80% $C_{14-16}$ Sodium α-olefin sulfonate (40% a.i.)
  4% Guar gum (Jaguar 7500 X)
  16% Water
Formulation 5:
  80% $C_{14-16}$ Sodium α-olefin sulfonate (40% a.i.)
  4% Xanthan gum (Rhodopol 23)
  16% Water
Formulation 6;
  80% $C_{14-16}$ Sodium α-olefin sulfonate (40% a.i.)
  5% Guar gum (Jaguar HP 140)
  15% Water
Formulation 7;
  80% $C_{14-16}$ Sodium α-olefin sulfoanate (40% a.i.)
  5% Xanthan gum (Kelzan D)
  18% Water Each Formulation as well as each comparative composition was diluted 1:100 with hard water (342 ppm) to prepare the foamable ready-to-use tank mixes. Foam was produced from each tank mix and the foam was placed in a 40° C. oven to test the foam life. The results are presented in Table 1.

TABLE 1

| Formulation No. or Comparative Composition | Foam Life (Minutes) |
| --- | --- |
| 1 | 60–68 |
| 2 | 48–55 |
| 3 | 47–55 |
| 4 | 46–57 |
| 5 | 53–60 |
| 6 | 44–55 |
| 7 | 64–75 |
| A | 23–29 |
| B | 35–43 |

Formulations 1 and 7 were also tested in direct sunlight; surface temperature 93° F. (34° C.), a temperature 80° F. (27° C.) with a slight breeze, and humidity in the range of 50–55%. The foam life for Formulation 1 was 63 minutes and for Formulation 7 was 52 minutes.

EXAMPLES 8–12

Examples of concentrate compositions of this invention are the following compositions 8 –12.
Composition 8
  37% Sodium lauryl ether sulfate (2–3 moles EO)
  4% $C_{14}$ Alcohol
  37% Polyacrylic acid, MW 2-300,000
  22% 2-Butoxyethanol Composition 9
- 15% $C_{14-16}$ Sodium α-olefin sulfonate (90% a.i.)
- 25% $C_{8-10}$ Ammonium ether sulfanate (2–3 moles EO)
- 5% $C_{14}$ Alcohol
- 22% Polyacrylic acid, MW 2-300,000
- 33% 2-Butoxyethanol Composition 10
- 55% $C_{14-16}$ Sodium α-olefin sulfonate (53.6% a.i.)
- 5% $C_{14}$ Alcohol
- 9% 2-Butoxyethanol
- 5% Diethylene glycol
- 6% Isopropanol
- 15% Polyacrylic acid, MW 2-300,000
- 5% Chelating agent (Briquest 1-dpa 60W)

Composition 11
- 44% Sodium lauryl ether sulfate (2–3 moles EO)
- 5% $C_{14}$ Alcohol
- 10% Ethylene oxide/propylene oxide block copolymer (ANTAROX F-88, MW 11, 400)
- 30% 2-Butoxyethanol
- 11% Water Composition 12
- 55% $C_{14-16}$ Sodium α-olefin sulfonate (53.6% a.i.)
- 5% $C_{14}$ Alcohol
- 10% 2-Butoxyethanol
- 4% Diethylene glycol
- 6% Isopropanol
- 15% Polyacrylic acid, MW 2-300,000
- 5% Chelating agent (Briquest 1-DPA 60W)

EXAMPLE 13

The stability against wind of the foam markers of this invention are demonstrated by the following examples in which marker foam of this invention and comparative marker foams were subjected to a wind stability test. In the wind stability test a fan operating in a cardboard tunnel was operated at a fan speed sufficient to produce a wind face velocity across foam dollops of about 600–700 ft/min. The time period until the foam dollop blows away is measured. In this test, procedure the afore-described Compositions 11 and 12 were employed. As the Comparative compositions there was employed Comparative Compositions C and D which correspond to, respectively, to Compositions 11 and 12 but where the ethylene oxide/propylene oxide of Composition 11 and the polyacrylic acid components of Compositions 11 and 12, respectively, have been replaced with additional water. Commercially available, heretofore mentioned, Comparative Composition B was also used on this test. Each composition was diluted 1:100 with tap water and foam marker dollops produced therefrom and subjected to the wind stability tests.

The results of the wind stability tests are set forth on Table 2.

TABLE 2

| Composition No. | Foam Blow Away Time (Minutes) |
|---|---|
| 11 | 30.9 |
| C | 20.3 |
| 12 | 25.9 |
| D | 14.5 |
| B | 14.3 |

EXAMPLE 14

The increased life, in outdoor conditions, of the foams from the foam marker compositions of this invention was demonstrated in the following test in which foams from Compositions 11, Comparative Composition C and commercially available Comparative Composition B were employed. Each composition was diluted 1:100 with tap water and foam marker dollops produced therefrom on outside soil where the surface temperatures ranged from 98–105° F. (37–41° C.), air temperature was 90° F. (32° C.) with a wind speed of about 5 mph under high humidity, sunny conditions. The test Results are set forth in Table 3.

TABLE 3

| Composition | Foam Life (Avg) in Minutes |
|---|---|
| 11 | 73.3 |
| C | 50.5 |
| B | 42.8 |

With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A foamable aqueous agricultural foam marker concentrate composition for dilution with about 100 parts by weight or more of water based on one part by weight of the concentrate, the foam marker concentrate comprising:

(a) about 10 to about 40 wt % of at least one anionic surfactant selected from the group consisting of salts of an α-olefin sulfonate having from about 12 to about 16 carbon atoms and salts of n alkyl ether sulfate having from 8 to about 16 carbon atoms;

(b) from about 4 to about 8 wt % of at least one linear alkanol having from about 12 to about 16 carbon atoms;

(c) from about 3 to about 20 wt % of a foam stabilizing polymer selected from the group consisting of a polyacrylic acid and salts thereof having a molecular weight of from about 10,000 to about 500,000, an ethylene oxide/propylene oxide block copolymer having a molecular weight up to about 30,000, a polyethylene glycol having a molecular weight of 400 or greater, and a biopolymer having a molecular weight of about 100,000 or greater; and (d) from about 5 to about 40% wt % of one or more solvents selected from the group consisting of 2-butoxyethanol, diethylene glycol, ethanol, propanol, isopropanol, and butanol;

wherein the weight percents are based on the total weight of the concentrate composition and the weight percent of the anionic surfactant is on a dry weight basis of the surfactant.

2. A foamable aqueous agricultural foam marker concentrate composition according to claim 1 wherein the anionic surfactant of component (a) is a sodium α-olefin sulfonate and the foam stabilizing polymer of component (c) is a polyacrylic acid or its salt.

3. A foamable aqueous agricultural foam marker concentrate composition according to claim 1 wherein the stabilizing polymer of component © is selected from the group consisting of a guar and xanthan gums.

4. A foamable aqueous agricultural foam marker concentrate composition according to claim 1 wherein the foam stabilizing polymer is a ethylene oxide/propylene oxide block copolymer.

5. A foamable aqueous agricultural foam marker concentrate composition according to claim 1 additionally comprising from about 1 to about 10 wt % of a chelating agent.

6. A ready-to-use aqueous agricultural foam marker formulation, the foam marker formulation comprising:
(a) about 0.10 to about 0.40 wt 5 of at least one anionic surfactant selected from the group consisting of salts of an α-olefin sulfonate having from about 12 to about 16 carbon atoms and salts of an alkyl ether sulfate having from about 8 to about 16 carbon atoms;
(b) from about 0.03 to about 0.20 wt % of a foam stabilizing polymer selected from the group consisting of a polyacrylic acid and salts thereof and having a molecular weight of from about 10,000 to about 500,000, an ethylene oxide/propylene oxide block copolymer having a molecular weight of up to about 30,000 a polyethylene glycol having a molecular weight of 400 or greater, and a biopolymer having a molecular weight of about 100,000 or greater;
(c) optionally from about 0.04 to about 0.08 wt % of at least one linear alkanol having from about 12 to about 16 carbon atoms;
(d) optionally from about 0.05 to about 0.40 wt % of one or more solvents selected from the group consisting of 2-butoxyethanol, diethylene glycol, hexylene glycol, dipropylene glycol, ethanol, propanol, isopropanol and butanol; and
(e) water;
wherein the weight percents are based on the total weight of the ready-to-use formulation and the weight percent of the anionic surfactant is on a dry weight basis of the surfactant.

7. A ready-to-use formulation according to claim 6 wherein optional components (c) and (d) are both present.

8. A ready-to-use formulation according to claim 6 wherein the anionic surfactant of component (a) is a sodium α-olefin sulfonate and the foam stabilizing polymer of component (c) is a polyacrylic acid or its salt.

9. A ready-to-use formulation according to claim 6 wherein the stabilizing polymer of component (c) is selected form the group consisting of a guar and xanthan gums.

10. A ready-to-use formulation according to claim 6 wherein the foam stabilizing polymer is a ethylene oxide/propylene oxide block copolymer.

11. A ready-to-use formulation according to claim 6 additionally comprising from about 0.01 to about 0.10 wt % of a chelating agent.

12. In a method of depositing a foam marker at the edge of an agricultural area being treated to distinguish treated area from untreated area, the improvement comprising depositing a foam marker produced from a ready-to-use formulation according to claim 6.

13. In a method of depositing a foam marker at the edge of an agricultural area being treated to distinguish treated area from untreated area, the improvement comprising depositing a foam marker produced from a ready-to-use formulation according to claim 7.

14. In a method of depositing a foam marker at the edge of an agricultural area being treated to distinguish treated area from untreated area, the improvement comprising depositing a foam marker produced from a ready-to-use formulation according to claim 8.

15. In a method of depositing a foam marker at the edge of an agricultural area being treated to distinguish treated area from untreated area, the improvement comprising depositing a foam marker produced from a ready-to-use formulation according to claim 9.

16. In a method of depositing a foam marker at the edge of an agricultural area being treated to distinguish treated area from untreated area, the improvement comprising depositing a foam marker produced from a ready-to-use formulation according to claim 10.

17. In a method of depositing a foam marker at the edge of an agricultural area being treated to distinguish treated area from untreated area, the improvement comprising depositing a foam marker produced from a ready-to-use formulation according to claim 11.

* * * * *